United States Patent
Kiehlbauch et al.

(10) Patent No.: US 7,402,156 B2
(45) Date of Patent: Jul. 22, 2008

(54) COUNTER PRESSURE DEVICE FOR OPHTHALMIC DRUG DELIVERY

(75) Inventors: Charles C. Kiehlbauch, Cleburne, TX (US); James E. Chastain, Fort Worth, TX (US); Daniel P. Leavitt, Leesport, PA (US); Randal L. Berardi, Ephrata, PA (US)

(73) Assignee: Alcon, Inc., Hunenberg (CH)

( * ) Notice: Subject to any disclaimer, the term of this patent is extended or adjusted under 35 U.S.C. 154(b) by 63 days.

(21) Appl. No.: 11/207,101

(22) Filed: Aug. 18, 2005

(65) Prior Publication Data
US 2006/0047255 A1   Mar. 2, 2006

Related U.S. Application Data

(60) Provisional application No. 60/606,376, filed on Sep. 1, 2004.

(51) Int. Cl.
| | |
|---|---|
| *A61M 35/00* | (2006.01) |
| *A61B 1/32* | (2006.01) |
| *A61B 18/18* | (2006.01) |
| *A61F 5/00* | (2006.01) |

(52) U.S. Cl. .................. 604/294; 600/236; 606/4; 606/204.25

(58) Field of Classification Search ............... 604/48, 604/264, 294–302, 521; 424/427–429; 600/398, 600/406, 236; 606/5, 107, 204.25, 4, 6, 161, 606/166; D24/120, 157
See application file for complete search history.

(56) References Cited

U.S. PATENT DOCUMENTS

| | | | | |
|---|---|---|---|---|
| 313,926 | A | * | 3/1885 | Deverall ..................... 215/307 |
| 4,540,408 | A | * | 9/1985 | Lloyd ......................... 604/294 |
| 6,001,386 | A | * | 12/1999 | Ashton et al. ............... 424/423 |
| 6,413,245 | B1 | | 7/2002 | Yaacobi et al. |
| 2008/0081952 | A1 | * | 4/2008 | Josephberg ................. 600/236 |

* cited by examiner

*Primary Examiner*—T. Zalukaeva
*Assistant Examiner*—Michael G Bogart
(74) *Attorney, Agent, or Firm*—W. David Lee

(57) ABSTRACT

A counter pressure device for ophthalmic drug delivery. The device includes a handle and a head coupled to a distal end of the handle. The head comprises a curved, concave surface for contacting the conjunctiva and having a notch for removably receiving a cannula. The device minimizes or prevents drug reflux and facilitates drug placement during ophthalmic drug delivery.

2 Claims, 2 Drawing Sheets

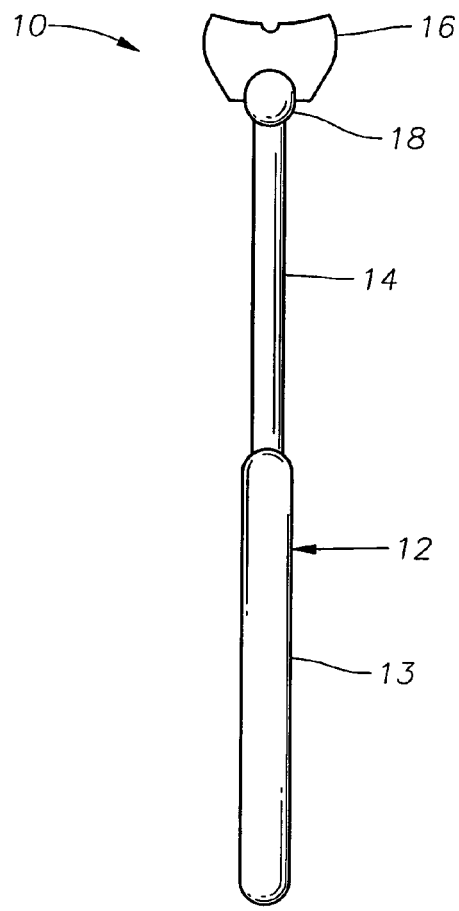
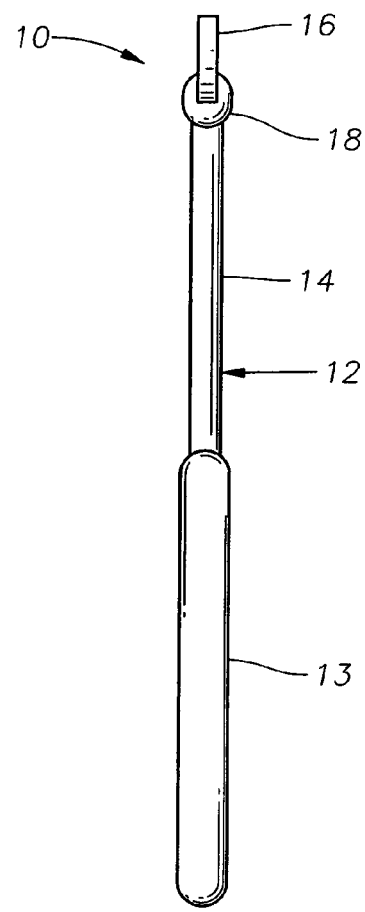
Fig. 1      Fig. 2
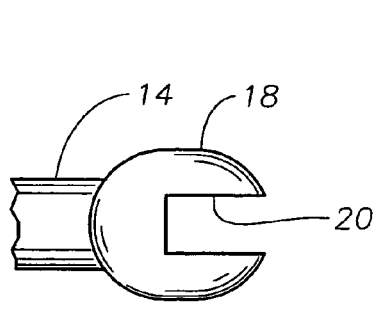
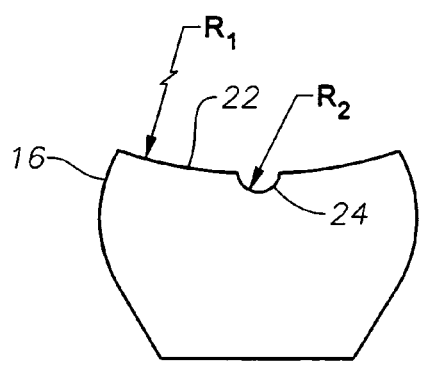
Fig. 3      Fig. 4

COUNTER PRESSURE DEVICE FOR OPHTHALMIC DRUG DELIVERY

This application claims the priority of U.S. Provisional Application No. 60/606,376 filed Sep. 1, 2004.

FIELD OF THE INVENTION

The present invention generally pertains to a counter pressure device for ophthalmic drug delivery. More particularly, but not by way of limitation, the present invention pertains to such a device for posterior segment ophthalmic drug delivery.

DESCRIPTION OF THE RELATED ART

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, glaucoma, and neuropathies are several examples.

ARMD is the leading cause of blindness in the elderly of developed countries. ARMD attacks the center of vision and blurs it, making reading, driving, and other detailed tasks difficult or impossible. About 200,000 new cases of ARMD occur each year in the United States alone. Current estimates reveal that approximately forty percent of the population over age 75, and approximately twenty percent of the population over age 60, suffer from some degree of macular degeneration. "Wet" ARMD is the type of ARMD that most often causes blindness. In wet ARMD, newly formed choroidal blood vessels (CNV) leak fluid and cause progressive damage to the retina.

In the particular case of CNV in ARMD, three main methods of treatment are currently being developed, (a) photocoagulation, (b) photodynamic therapy, and (c) the use of angiogenesis inhibitors. Photocoagulation is the most common treatment modality for CNV. However, photocoagulation can be harmful to the retina and is impractical when the CNV is near the fovea. Furthermore, over time, photocoagulation often results in recurrent CNV. Photodynamic therapy is a relatively new technology. The long-term efficacy of photodynamic therapy to treat ARMD is still largely unknown. Oral or parenteral (non-ocular) administration of anti-angiogenic compounds is also being tested as a systemic treatment for ARMD. However, due to drug-specific metabolic restrictions, systemic administration usually provides sub-therapeutic drug levels to the eye. Therefore, to achieve effective intraocular drug concentrations, either an unacceptably high dose or repetitive conventional doses are required.

Various needles and cannulae have been used to deliver drugs to the back of the eye, external to the globe. Examples of such needles and cannulae are disclosed in U.S. Pat. No. 6,413,245 and the references cited therein. U.S. Pat. No. 6,413,245 discloses preferred cannulae for sub-Tenon, juxtascleral delivery of a drug depot to the posterior segment of a human eye and is incorporated herein in its entirety by this reference. When these cannulae are used to create such a drug depot, drug reflux may sometimes occur during or immediately after administration.

A need remains in the field of ophthalmology for improved devices for the administration of an ophthalmic drug, especially to the posterior segment of the eye. In particular, improved devices are needed to minimize or prevent drug reflux as described above, and to facilitate drug depot placement. These improved devices should be safe for the patient, should be easy for the physician to use, and should improve the efficacy of drug administration.

SUMMARY OF THE INVENTION

One aspect of the present invention is a counter pressure device for ophthalmic drug delivery. The device includes a handle and a head coupled to a distal end of the handle. The head comprises a curved, concave surface for contacting the conjunctiva and having a notch for removably receiving a cannula. The device minimizes or prevents drug reflux and facilitates drug placement during ophthalmic drug delivery.

BRIEF DESCRIPTION OF THE DRAWINGS

For a more complete understanding of the present invention, and for further objects and advantages thereof, reference is made to the following description taken in conjunction with the accompanying drawings in which:

FIG. 1 is a front view of a counter pressure device according to a preferred embodiment of the present invention;

FIG. 2 is a side view of the counter pressure device of FIG. 1;

FIG. 3 is an enlarged, fragmented, side view of the retaining member of the distal extension of the counter pressure device of FIG. 1;

FIG. 4 is an enlarged, front view of the head of the counter pressure device of FIG. 1.

DETAILED DESCRIPTION OF THE PREFERRED EMBODIMENTS

Figure 5:
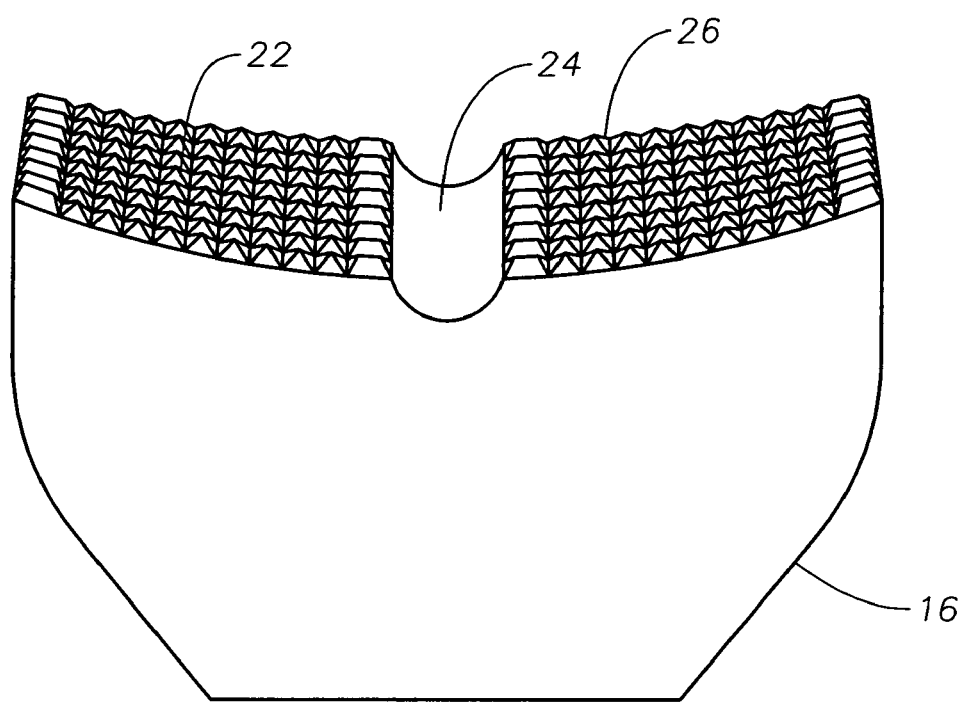
FIG. 5 is an enlarged, front perspective view of the head of the counter pressure device of FIG. 1.

The preferred embodiments of the present invention and their advantages are best understood by referring to FIGS. 1-5 of the drawings, like numerals being used for like and corresponding parts of the various drawings.

Counter pressure device 10 preferably includes a handle 12 and a head 16. As shown in the Figures, handle 12 has a grip 13 and a distal extension 14. Grip 13 is preferably made of a conventional polymer such as polyethylene or polypropylene and has a length of about 3 cm. Distal extension 14 is preferably integrally formed with grip 13 and is preferably made of conventional polymer such as polyethylene or polypropylene. Distal extension 14 preferably has a length of about 2.5 cm. Distal extension 14 has a retaining member 18 formed on its distal end. Retaining member 18 has a slot 20 for frictionally coupling head 16. Head 16 has a curved, concave surface 22 for contacting a conjunctiva of an eye and conforming to the curvature of the eye. For the human eye, surface 22 preferably has a radius of curvature $R_1$ of about 10 mm to about 14 mm, and most preferably 12 mm. Surface 22 preferably has a texture 26. Preferred textures for texture 26 include a 16-20 μin finish; a MT-1150 finish available from Mold-Tech of Youngstown, Ohio; or an MT-1160 finish available from Mold-Tech. Surface 22 may alternatively have knurls 26. Surface 22 preferably also has a centrally disposed notch 24 for removably receiving a cannula. As used herein, the term "cannula" refers to both a blunt-tipped cannula and a sharped-tip needle, unless otherwise noted. Notch 24 preferably has a radius of curvature $R_2$ of about 0.2 mm to about 1 mm, and most preferably 0.56 mm. Notch 24 preferably has a depth (in the longitudinal direction of device 10) of about 0.1 mm to about 2 mm, and most preferably 0.56 mm. Head 16 preferably has a height (in the longitudinal direction of device 10) of about 4 mm to about 6 mm, and most preferably 5.7 mm; a width of about 8 mm to about 10 mm, and most preferably about 8.5 mm, and a thickness (when viewed as shown in FIG. 2) of about 1.2 mm to about 3 mm, and most preferably about 1.3 mm. The thickness of head 16 is designed for frictionally coupling with slot 20. Head 16 is preferably formed from a foam or rubber-like material. The foam or rubber-like material is preferably non-absorbent or minimally absorbent and is firm but compliant (not hard). A preferred material is silicone. Another preferred material is cellulose, and more preferably compressed cellulose. Most preferably, the compressed cellulose is sterilized using gamma radiation, which makes the cellulose more firm and less absorbent.

The following describes a preferred procedure by which a physician may use counter pressure device 10 to minimize or prevent drug reflux during sub-Tenon, juxtascleral delivery of a drug depot to the posterior segment of a human eye using a cannula. Preferred cannulae for such drug delivery are disclosed in U.S. Pat. No. 6,413,245. In the superior temporal quadrant of the eye, the physician uses fine scissors to create a small incision in the conjuctiva and Tenon's capsule to bare sclera at a point about 8 mm to about 9 mm posterior to the limbus. The cannula used to deliver the drug is then inserted through the incision. The distal tip of the cannula is advanced along the curvature of the sclera until the tip is located in the desired position. The physician then grasps device 10 via grip 13 of handle 12. Using handle 12, the physician preferably positions device 10 so that device 10 is perpendicular to the conjunctiva, so that surface 22 of head 16 is perpendicular to and in contact with the conjunctiva posterior to the incision, and so that the cannula is positioned within notch 24. When disposed in notch 24, the cannula is preferably perpendicular to head 16 of device 10. While using handle 12 to apply pressure to the conjunctiva via head 16, the physician slowly injects the drug to create a drug depot on the outer surface of sclera below the Tenon's capsule. Texture 26, or knurls 26, prevents surface 22 from slipping during contact with the conjunctiva. While continuing to apply pressure with device 10, the physician slowly withdraws the cannula from the incision. After withdrawal, the physician continues to apply pressure with device 10 for an additional time period of about 5 seconds. The physician then removes device 10, applies an antibiotic ointment, and optionally applies a pressure patch to the incision. The geometry of device 10 allows the physician to effectively apply pressure proximate to, and preferably posterior to, the incision to counter the tendency of certain drug depots to reflux.

From the above, it may be appreciated that the present invention provides an improved device for the administration of an ophthalmic drug, especially to the posterior segment of the eye. In particular, the device of the present invention minimizes or prevents drug reflux and facilitates drug placement during ophthalmic drug delivery. The device is safe for the patient, easy for the physician to use, and improves the efficacy of drug administration.

The present invention is illustrated herein by example, and various modifications may be made by a person of ordinary skill in the art. For example, although the device of the present invention is described above in connection with preventing reflux in sub-Tenon, juxtascleral delivery of a drug depot to the posterior segment, it can also be utilized in connection with other ophthalmic drug delivery. As another example, device 10 may be formed with a longer grip 13, a retaining member 18 coupled to grip 13, and a head 16 but without distal extension 14, if desired.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A counter pressure device for minimizing drug reflux during ophthalmic drug delivery with a cannula, comprising:
    a handle;
    a head coupled to a distal end of said handle, said head comprising a curved, concave surface for contacting a conjunctiva and a notch centrally disposed on said curved, concave surface for removably receiving a cannula, wherein:
    said head is made of silicone;
    said curved, concave surface has a radius of curvature of about 10 mm to about 14 mm and a thickness of about 1.2 mm to about 3 mm;
    said notch has a radius of curvature of about 0.2 mm to about 1 mm; and
    a portion of said curved, concave surface outside of said notch is formed with a slippage preventing texture comprising a plurality of knurls, each of said knurls having a pyramidal geometry.

2. The counter pressure device of claim 1 wherein said radius of curvature of said curved, concave surface is about 12 mm.

\* \* \* \* \*